(12) United States Patent
Jones et al.

(10) Patent No.: US 6,995,148 B2
(45) Date of Patent: Feb. 7, 2006

(54) ADENOSINE CYCLIC KETALS: NOVEL ADENOSINE ANALOGUES FOR PHARMACOTHERAPY

(75) Inventors: Garth S. Jones, Pittsburgh, PA (US); Edwin K. Jackson, Pittsburgh, PA (US)

(73) Assignee: University of Pittsburgh, Pittsburgh, PA (US)

(*) Notice: Subject to any disclaimer, the term of this patent is extended or adjusted under 35 U.S.C. 154(b) by 375 days.

(21) Appl. No.: 09/828,276

(22) Filed: Apr. 5, 2001

(65) Prior Publication Data

US 2002/0147174 A1 Oct. 10, 2002

(51) Int. Cl.
*C07D 473/34* (2006.01)
*C07D 471/04* (2006.01)
*A61K 31/52* (2006.01)

(52) U.S. Cl. ............... 514/45; 514/44; 514/46; 514/231.5; 514/356; 536/23.1; 536/27.62; 536/27.6; 536/22.1; 536/27.7; 536/120; 435/6; 546/296; 544/242; 544/296; 544/277

(58) Field of Classification Search ............... 536/27.6, 536/22.1, 27.62, 27.7, 23.1, 120; 544/242, 544/296, 277, 303, 317; 514/44, 45, 46, 231–235, 514/356; 435/6; 546/296

See application file for complete search history.

(56) References Cited

U.S. PATENT DOCUMENTS

| | | | | |
|---|---|---|---|---|
| 4,167,565 A | * | 9/1979 | Stein et al. ............ | 424/180 |
| 4,968,672 A | | 11/1990 | Jacobson et al. | |
| 5,861,405 A | | 1/1999 | Jacobson et al. | |
| 5,998,388 A | * | 12/1999 | Ellis et al. ............ | 514/46 |
| RE37,045 E | * | 2/2001 | Olsson et al. ............ | 514/46 |
| 6,294,522 B1 | * | 9/2001 | Zablocki et al. ......... | 514/46 |
| 6,376,472 B1 | * | 4/2002 | Myers et al. ............ | 514/44 |
| 6,407,076 B1 | * | 6/2002 | Box et al. ............ | 514/46 |

OTHER PUBLICATIONS

Vidt, D.G. *In:* Goodfriend T.L. et al., Eds., Hypertensive primer, 2$^{nd}$ ed., (1999) p. 437–442.
Drury and Szent–Gyorgyi J. Phys. 1929 68:213–237.
Jacob, M.I. and Berne, R.M. Am. J. Phys. 1960; 198: 322.
Jacobson, K.A. et al. J. Medicinal Chem. 1992; 35:407–422.
Jacobson, K.A. et al. Mol. Pharm. 1985; 29: 126–133.
Bridges, A.J. et al. J. Medicinal Chem. 1988; 31:1282–1285.
Jarvis, M.F. et al. J. Pharm. Exp. Ther. 1989; 251: 888–893.
Fuetes, M. et al. J. Org. Chem. 1976; 41: 4074–4077.
Devasagayaraj, A. and Knochel, P. Tetrahedron Lett. 1995; 36: 8411–8414.
Klein, H. and Neff, H. Angewandte Chemie 1956; 68: 681–682.
Tamaru, X. et al. Angewandte Chemie, Int. Ed. English 1987; 26: 1157–1158.
Knoess, H.P. et al. J. Org. Chem., 1991; 56: 5974–5978.

* cited by examiner

*Primary Examiner*—James O. Wilson
*Assistant Examiner*—Devesh Khare
(74) *Attorney, Agent, or Firm*—Reed Smith LLP

(57) ABSTRACT

The present invention relates to novel compounds that are novel adenosine receptor analogues. Specifically, the compounds of the present invention preferably function as both adenosine receptor agonists and ganglionic blocking agents. To achieve this functionality, the compounds of the present invention, preferably contain a ganglionic blocking motif, is inserted into the adenosine molecule. The ganglionic blocking motif preferably includes an elongated carbon chain that, in a particularly preferred embodiment, contains two terminal amino groups. The ganglionic blocking motif preferably includes a carbon along the elongated carbon chain that is integral to a cyclic ketal that is part of the adenosine molecule. In presently-preferred embodiments, the elongated carbon chain ranges from two to sixteen carbons in length. The compounds of the present invention will be useful for treatment of a variety of conditions including, but not limited to, hypertension, vasodilation, and ischemia.

17 Claims, 7 Drawing Sheets

ADENOSINE CYCLIC KETAL (ACK)

AND $R_3$, $R_4$ AND $R_5$ = HYDROGEN

CHEMICAL STRUCTURE OF ADENOSINE CYCLIC KETAL (ACK) AND THE CHEMICAL FORMULA OF THE COMPOUND NONAMETHONIUM ADENOSINE CYCLIC KETAL (NONAMETHONIUM ACK).

ADENOSINE CYCLIC KETAL (ACK)

WHEN $R_1 = R_2 =$

AND $R_3$, $R_4$ AND $R_5$ = HYDROGEN

AND $R_6 =$

CHEMICAL STRUCTURE OF ADENOSINE CYCLIC KETAL (ACK) AND THE CHEMICAL FORMULA OF THE COMPOUND NONAMETHONIUM ADENOSINE CYCLIC KETAL (NONAMETHONIUM ACK).

The synthetic scheme for synthesizing nonamethonium adenosine cyclic ketal.
The reagents and conditions are: i) zinc dust, tetrahydrofuran (THF);
ii) N-methylpyrrolodine, CoBr$_2$, carbon monoxide;
iii) adenosine, HCl/dioxane, (EtO)$_3$CH, DMF; iv) 40% Me$_3$N in H$_2$O.

ADENOSINE CYCLIC KETALS: NOVEL ADENOSINE ANALOGUES FOR PHARMACOTHERAPY

FIELD OF THE INVENTION

The present invention is directed to a novel class of adenosine-based therapeutic agents which are useful for a wide range of clinical applications including, but not limited to, those involving hypertension, vasodilation and ischemia.

BACKGROUND OF THE INVENTION

Vasodilators are used in coronary artery disease to increase blood flow to damaged or ischemic tissue; they are similarly used for treating strokes often resulting in major improvements in a patient. However, undesirable side effects present a drawback to vasodilators currently in use. For example, sodium nitroprusside causes thiocyanate intoxication, methemoglobinemia, acidosis and cyanide poisoning according to Vidt, D. G. In: Goodfriend T.L. et al., Eds., Hypertensive primer, $2^{nd}$ Ed., (1999) pp. 437–442. Additionally, sodium nitroprusside is extremely light sensitive such that the intravenous (IV) delivery sets carrying it must be light resistant. Glyceryl trinitrate has side effects which include vomiting, flushing, headache and methemoglobinemia. Use of this compound requires a special delivery system to prevent binding of the drug to the infusion line. Many of the currently available drugs including sodium nitroprusside, glyceryl trinitrate, diazoxide, fenoldopam, hydralazine, nicardipine and phentolamine cause marked tachycardia due to reflex activation of the sympathetic nervous system as described by Vidt, D. G. supra. Tachycardia increases myocardial oxygen demand and thus may worsen myocardial ischemia. Other rapidly acting vasodilators such as verapamil, labetalol and esmolol slow cardiac conduction and may cause heart block.

Many currently-employed drugs such as nicardipine, verapamil, diazoxide, hydralazine and labetalol display slow offset of action which makes the dose titration difficult. Even fenoldopam and esmolol have an offset of action of 15 to 30 minutes. None of the currently available rapid-onset/-offset vasodilators preferentially protects blood flow to all of the vital organs (brain, heart, kidneys and gut); nor do the currently available vasodilators have the beneficial ancillary actions that could reduce the risk of cardiovascular events.

Thus, there is a need for drugs which act specifically as vasodilators, lack the undesirable characteristics of prolonged half-life with the induction of tachycardia and protect blood flow to vital organs. Activators of adenosine $A_{2A}$ receptors have potential as vasodilators which lack many of these undesirable side-effects.

Adenosine is an important neuromodulator in the central and peripheral nervous systems of mammals. As a neuromodulator, adenosine alters the rate at which a nerve cell fires. Peripherally, adenosine is likely to be either constitutively released, or released at times of high or low metabolic activity. Importantly, neuromodulators such as adenosine may act pre- or post-synaptically and may be subsequently taken up or metabolized.

The physiological effects of adenosine were first noted by Drury and Szent-Gyorgyi in J. Physiol. 68: 213–237 (1929). This study reported that extracts from various tissues including heart muscle, brain, kidney and spleen had profound effects on cardiovascular parameters. Further investigation revealed that the active substance in the tissue extracts was adenosine. Following this finding, investigation of the effects of adenosine on the cardiovascular system continued for the next 20 years. Beginning in the 1950's and continuing into the early 1960's, Berne and colleagues investigated the effects of adenosine on coronary blood flow as described in Jacob, M. I. and Berne, R. M. Amer. J. Physiol 198:322 (1960). This work led to the hypothesis that cardiac adenosine production plays an important role in the metabolic regulation of coronary blood flow, an hypothesis that has been expanded to include other organs including the brain and kidneys.

Currently, there are at least four known subtypes of adenosine receptors including the $A_1$, $A_{2A}$, $A_{2B}$ and $A_3$ receptors which have been cloned from animal or human sources. Adenosine receptors are members of the G-protein coupled receptor (GPCR) superfamily and mediate the stimulation or inhibition of adenylyl cyclase activity, and hence cyclic adenosine monophosphate levels. Adenosine receptors are currently the smallest cloned members of the GPCR superfamily.

Adenosine receptors are involved in a vast number of peripheral and central regulatory mechanisms including vasodilation, cardiac depression, inhibition of lipolysis, inhibition of insulin release and potentiation of glucagon release in the pancreas, inhibition of vascular smooth muscle cell growth, stimulation of endothelial cell growth, angiogenesis, wound healing and inhibition of neurotransmitter release from nerve terminals. A well-known class of adenosine receptor antagonists encompasses xanthines that include caffeine and theophylline which are commonly found in tea, coffee and cocoa. Adenosine itself has been used in the treatment of supraventricular tachycardia and may also be utilized as a diagnostic tool in the study of cardiac abnormalities.

Subsequent to the characterization of these adenosine receptors, research has focused on developing pharmacotherapeutic agents that are selective for one of the adenosine receptor subtypes. Consequently, a large array of highly selective drugs for adenosine $A_1$ and $A_{2A}$ receptors has been synthesized as described by Jacobson, K. A. et al. in J. Medicinal Chem. 35:407–422 (1992).

A number of selective analogues of adenosine receptor antagonists and agonists have been developed through a designer approach referred to as "functionalized congener" synthesis as described in U.S. Pat. No. 4,968,672 to Jacobson, as well as in Jacobson et al., Mol. Pharm. 29: 126–133 (1985), both of which are incorporated herein by reference in their entirety for methods and background relating to functionalized congener synthesis. Utilizing this method, analogues of adenosine receptor ligands bearing functionalized chains have been synthesized and attached covalently to various organic moieties such as amines and peptides. Attachment of polar groups to xanthine congeners has been found to increase water solubility.

Presently, the majority of $A_1$ and $A_{2A}$ receptor agonists are derivatives of adenosine. For example, numerous modifications of the $N^6$-position on adenosine with hydrophobic functionalities have yielded highly selective $A_1$ receptor agonists such as $N^6$-cyclopentyladenosine, $N^6$-cyclohexyladenosine, and $N^6$-phenylisopropyladenosine. Generally, $N^6$-substituted adenosine derivatives are selective for the $A_1$ receptor; however, some $N^6$-substituted adenosine analogs are highly potent $A_{2A}$ receptor agonists, e.g., $N^6$-[2-(3,5-dimethoxyphenyl)-2-(2-methylphenyl)ethyl] as described by Bridges, A J. et al. J. Medicinal Chem. 31: 1282–1285 (1988). Although modifications to the purine ring usually lead to lower activity, an exception is 1-deazaadenosine which retains high affinity for adenosine receptors. The 2-position of adenosine has also been modified in order to produce selective adenosine receptor agonists. CV 1808, a 2-arylamino adenosine analog described by Jarvis, M. F. et al. J. Pharmacol. Exp. Ther. 251:888–893 (1989) has modest affinity and selectively for $A_{2A}$ receptors. Additional 2-position modifications led to the generation of 2-alkoxyadenosines and 2-alkynyladenosines, some of which are potent $A_{2A}$ receptor agonists.

Selected ribose modifications have also generated potent $A_{2A}$ receptor agonists. For example, placement of an amide in the 5'-position of the ribose created adenosine-5'-N-ethyluronamide, which has greater potency at $A_{2A}$ receptors compared with adenosine, yet still retains $A_{2A}$ receptor agonist activity. Further modification on the 2-position of adenosine-5'-N-ethyluronamide led to the discovery of 2-[4-[(2-carboxyethyl)phenyl]ethylamino]-5'-N-ethylcarboxamidoadenosine, also known as CGS 21680 as described by Jarvis et al., supra. CGS 21680 is not only 140-fold more selective for the $A_{2A}$ versus the $A_1$ receptor, but also exhibits a high affinity for $A_{2A}$ receptors while exhibiting no affinity for $A_{2B}$ receptors. Although thio-substitution for the 4'-oxygen in 2-chloroadenosine enhanced affinity for $A_{2A}$ receptors, other ribose modifications have resulted in decreased activity at adenosine receptors. In particular, substitutions at 2'- and 3' positions appear to nearly always reduce activity.

SUMMARY OF THE INVENTION

An embodiment of the present invention includes analogues of adenosine cyclic ketal (ACK) of the formula:

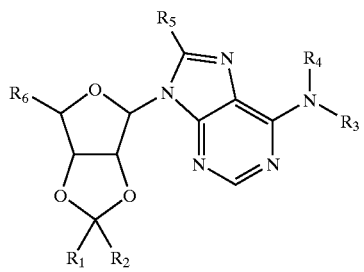

wherein $R_1$ $R_2$, $R_3$, $R_4$, $R_5$ and $R_6$ are each chemical residues.

A more preferred embodiment of the present invention is the above compound wherein $R_1$ and $R_2$ are hydrogen.

A further preferred embodiment of the present invention is a compound of the above formula where $R_1$ and $R_2$ are alkyl groups which includes straight chains, branched and cyclic alkyl groups.

A further embodiment of the present invention is a compound of the above formula where $R_1$ and $R_2$ each may contain from one to thirteen carbons.

A yet further embodiment of the present invention is a compound of the above formula where the $R_1$ and $R_2$ groups each may be substituted with amine groups which include primary, secondary, tertiary and quaternary amines.

An even further embodiment of the present invention is a compound of the above formula where $R_1$ and $R_2$ are alkyl groups having from one to thirteen carbons that have an amine group substitution on the terminal carbon.

A still further embodiment of the present invention is a compound of the above formula where $R_5$ is a halogen such as fluorine, chlorine, or bromine.

An additional embodiment of the present invention is a compound of the above formula where $R_6$ is an alkyl alcohol group of the group methyl alcohol, ethyl alcohol, isopropyl alcohol and n-propyl alcohol.

A further embodiment of the present invention is a compound of the above formula where $R_6$ is a N-alkylcarboxamido group selected from the group consisting of N-methylcarboxamido, N-ethylcarboxamido, N-isopropylcarboxamido, and N-n-propyl carboxamido.

An even more preferred embodiment of the present invention includes analogues of adenosine cyclic ketal (ACK) of the formula:

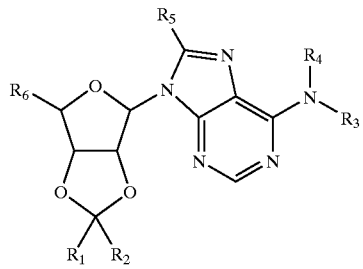

wherein $R_1$, $R_2$, are each

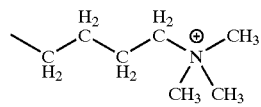

$R_3$, $R_4$, and $R_5$ are each hydrogen; and $R_6$ is

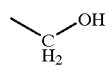

An additional embodiment of the present invention includes a pharmaceutical composition comprising an $A_{2A}$ adenosine receptor agonist that is an analogue of ACK along with a pharmaceutically acceptable carrier.

A further embodiment of the present invention includes a pharmaceutical composition for treating hypertension in a mammal comprising an antihypertensive effective amount of an ACK analogue together with a pharmaceutically acceptable carrier.

An additional embodiment of the present invention includes a method for treating hypertension in a mammal suffering therefrom comprising administering to such a mammal an antihypertensive effective amount of an ACK analogue in unit dosage form.

Furthermore, the present invention includes a method for protecting tissues and organs from ischemic damage comprising administering an effective amount of an ACK analogue with a pharmaceutically acceptable carrier in unit dosage form.

Yet another embodiment of the present invention includes a method for controlling vasodilation in a mammal comprising administering an effective amount of an ACK analogue. Additionally, this method includes reducing the risk of cardiovascular events.

The present invention also broadly encompasses a method of diagnostic imaging utilizing an ACK analogue.

The present invention also encompasses a group of compounds that block sympathetic outflow while also activating $A_{2A}$ receptors.

The present invention also broadly encompasses providing a therapeutic amount of an ACK analogue to treat a patient through a delivery system including chemical supplementation for therapeutic or prophylactic use in a subject in need thereof. A therapeutic amount of an ACK analogue is an amount that will prevent, alleviate or eliminate the symptoms associated with the particular disorder of the subject.

The present invention and its preferred embodiments will be better understood by way of reference to the detailed disclosure and to the accompanying drawings described hereinafter.

DETAILED DESCRIPTION OF THE PRESENT INVENTION

Figure 1A:
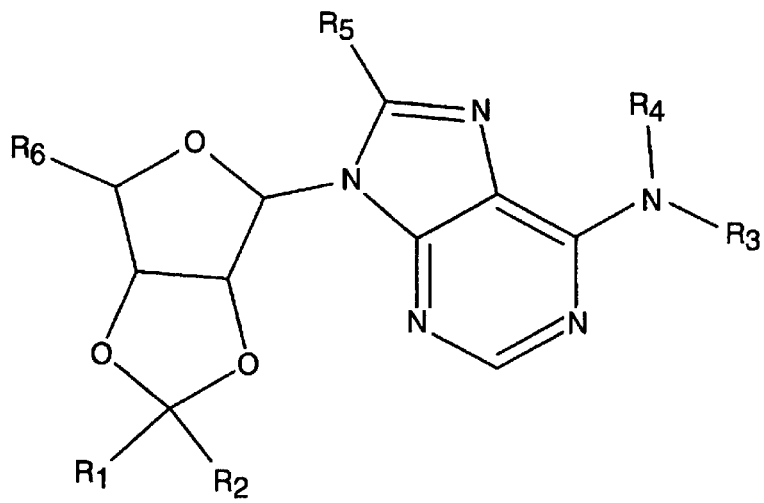
FIG. 1A shows the general chemical structure of adenosine cyclic ketal (ACK), the specific structure of nonamethonium ACK, a preferred embodiment of the a present invention.
Figure 1A:
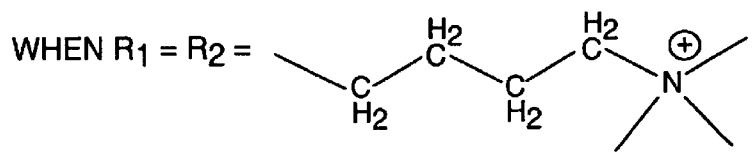

The present invention relates to novel compounds useful for a wide range of clinical applications including those involving hypertension, vasodilation and ischemia. Specifically, the compounds of the present invention function, in part, as adenosine $A_{2A}$ receptor agonists. In an embodiment of the present invention, the novel adenosine receptor agonists exhibit many of the desired properties of a rapid-onset/-offset vasodilator including one or more of the following: 1) exhibiting a half-life of seconds so that steady-state levels may be obtained quickly and drug action can be terminated rapidly; 2) failing to induce reflex tachycardia in order to prevent increased myocardial oxygen demand; 3) exhibiting preferential vasodilation of the brain, heart, kidney and gut circulation in order to protect these vital organs from hypotension-induced ischemia; 4) lacking light sensitivity and failing to bind to plastic tubing; 5) lacking effects on the cardiac conduction system thus avoiding heart block and other dysfunctions of cardiac conduction; 6) lacking toxic effects unrelated to vasodilation; and 7) possessing antiplatelet activity and protecting endothelial cells from damage, thus helping to reduce the risk of cardiovascular events.

Advantages of selective adenosine $A_{2A}$ receptor activation

Selective activation of $A_{2A}$ receptors, through use of the novel compounds of the present invention, markedly reduces arterial blood pressure. This effect is mediated by a reduction in peripheral vascular resistance while cardiac output is preserved. $A_{2A}$ receptor activation strongly dilates coronary, cerebral, mesenteric and renal vascular beds so that blood flow to these organs (i.e., heart, brain, gut and kidneys) is increased, or at least unchanged, despite reductions in arterial perfusion pressure. The coronary vasculature is particularly responsive to $A_{2A}$ receptor agonists. In this vascular bed, $A_{2A}$ receptor activation can increase coronary blood flow several fold. $A_{2A}$ receptor activation also attenuates platelet aggregation and adhesion and also reduces the ability of neutrophils to adhere to and damage vascular endothelial cells. $A_{2A}$ receptor activation, unlike administration of adenosine per se, has no direct effect on cardiac conduction. In addition, the "stress reaction" (chest pain, dyspnea, anxiety, etc.) associated with adenosine is mediated by $A_1$, not $A_{2A}$, receptors.

To prepare the adenosine receptor agonists of the present invention, a functionalized chain is inserted at a site in the pharmacophore, according to the functionalized congener approach of Jacobson et al., supra, but in a region of the adenosine molecule previously considered critical for activity.

The present adenosine receptor agonists are designed to act as rapid-onset/-offset vasodilators that increase blood flow to the brain, heart, gut and kidneys without causing reflex tachycardia and also to reduce the risk of cardiovascular events. The $A_{2A}$ receptor agonists of the present invention have the desired features for rapid-onset/-offset vasodilation, and have been modified to reduce the somewhat prolonged half-life and the adverse effect on heart rate due to induction of reflex tachycardia. It was discovered that insertion of a ganglionic blocking motif, such as a quaternary amine group, into the adenosine molecule would reduce and even eliminate the two unwanted side effects associated with previous $A_{2A}$ receptor agonists, namely increased heart rate and induction of reflex tachycardia. Specifically, inserting a ganglionic blocking motif into the adenosine molecule activates adenosine $A_{2A}$ receptors while also blocking the activity of the autonomic nervous system. Activation of adenosine $A_{2A}$ receptors with the agonists of the present invention reduces arterial blood pressure, while the autonomic system blockade serves to prevent reflex tachycardia, as well as to augment the hypotensive actions induced by stimulation of adenosine $A_{2A}$ receptors.

Synthesis and design of an ACK analogue nonamethonium ACK

The ganglionic blocker hexamethonium, which comprises two quaternary amines separated by a linear chain of six methylenes, has a relatively simple structure making a "hexamethonium mimetic" a promising choice to insert into the adenosine molecule. An important consideration in the design of the analogues of the present invention was that the adenosine analogue be rapidly inactivated by adenosine deaminase so that the plasma half-life would be short -similar to that of naturally occurring adenosine. Major sites on the adenosine molecule that can be modified while retaining adenosine receptor activity are the N-6', 2' and 5' positions. However, substitutions at these three sites could markedly impair deamination by adenosine deaminase since these positions are located on the end of the adenosine molecule which interacts with the active site of adenosine deaminase. On the other hand, the 2'-and 3'-hydroxyls are remote from the deamination site and are more likely to allow for modification in the creation of novel synthetic adenosine receptor agonists without hindering deamination.

Figure 1B:
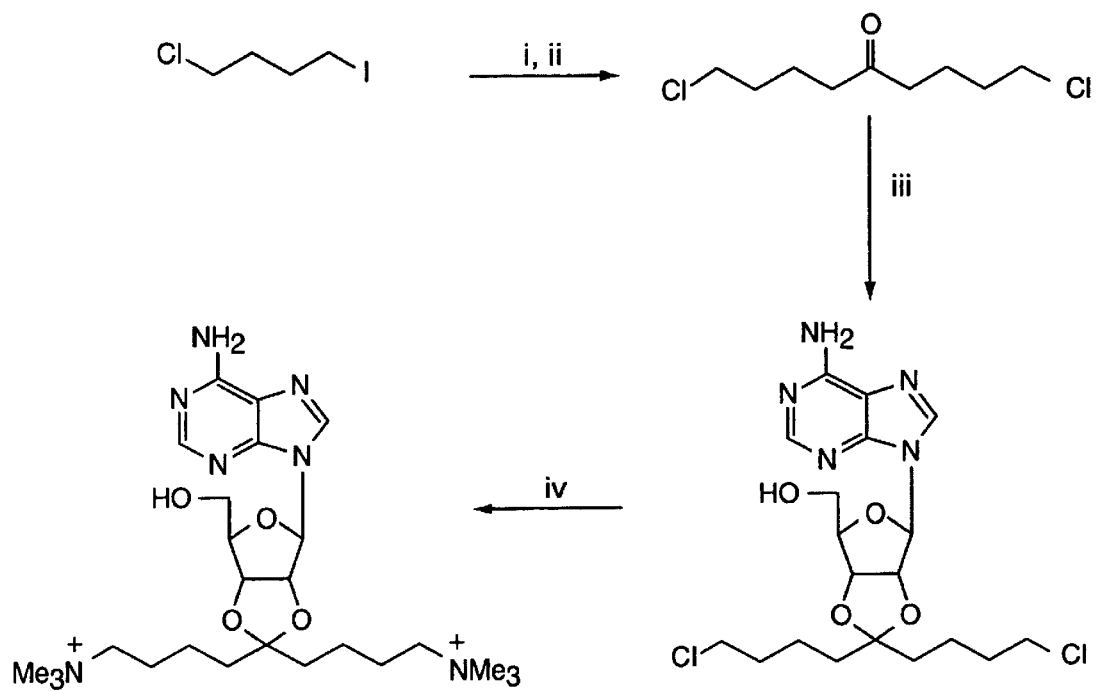
FIG. 1B illustrates the synthetic scheme used to synthesize nonamethonium ACK.
Figure 2A:
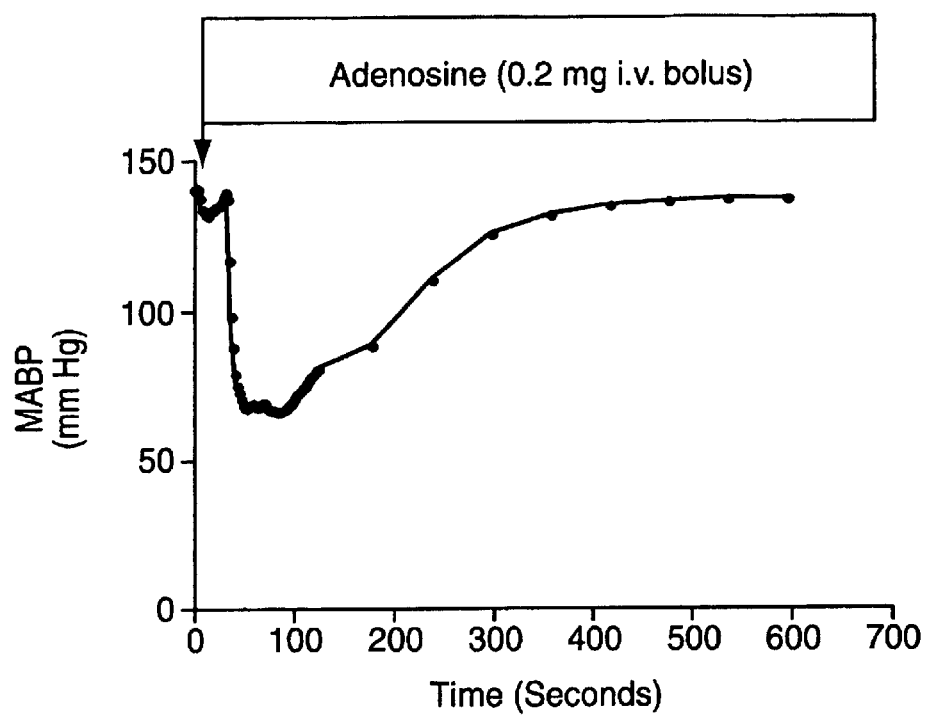
FIG. 2A is a graph illustrating the effects of an intravenous bolus of adenosine (0.2 mg/kg) on mean arterial blood pressure in anesthetized rat.
Figure 2B:
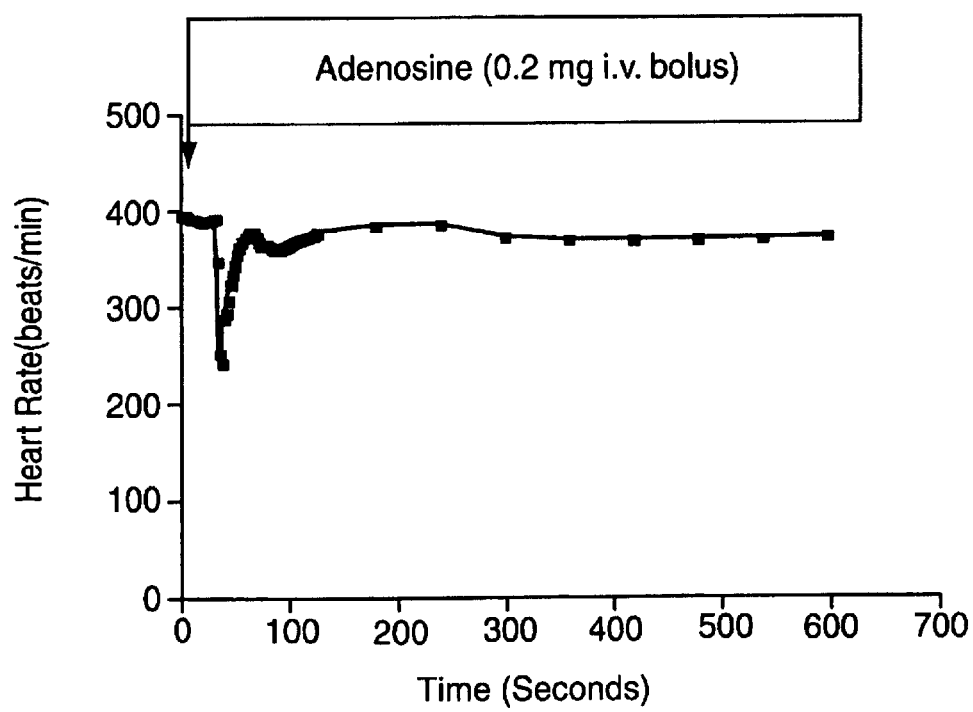
FIG. 2B is a graph illustrating the effects of an intravenous bolus of adenosine (0.2 mg/kg) on heart rate in anesthetized rat.

The novel adenosine receptor agonists of the present invention are prepared by modifying a cyclic ketal, as shown in FIG. 1A and FIG. 1B, to have the 2'-and 3'-hydroxyls linked by a single carbon atom. By placing the carbon atom of the cyclic ketal in the middle of the "hexamethonium mimetic," it was reasoned that the desired ganglionic blocking activity of the "hexamethonium mimetic" would be maintained. Additionally, rather than using hexamethonium as the "hexamethonium mimetic," embodiments of the present invention have an elongated carbon chain length of nine carbons, thus comprising a "nonamethonium mimetic". Extending the carbon chain length alleviates possible steric effects on the cyclic ketal side chains. As described in detail below, nonamethonium ACK exhibits many desired pharmacological properties. Additional variations/forms of these molecules including alkylmethonium ACKs of various spacer distances between the quaternary ammonium groups will be expected to exhibit similar desired properties.

The adenosine cyclic ketal of the present invention was synthesized as shown schematically in FIG. 1B. Adenosine may be ketalized at the 2' and 3' positions by treating the nucleoside with the desired ketone (such as 1,9-dichlorononan-5-one) in the presence of anhydrous acid and triethylorthoformate according to Fuertes, M. et al. J. Organic Chem. 41: 4074–4077 (1976), which is incorporated herein by reference in its entirety. Anhydrous HCl gas bubbled through dry dioxane gave the best results using anhydrous dimethylformamide (DMF) as the solvent. Thus, it was possible to ketalize adenosine with dichloroketone in modest yield. Dichloroketone was prepared by two methods, the second of which is more general and preferred. In the first method, 4-chloro-1-iodopropane was converted to the corresponding akyl zinc reagent and then that organometallic compound was treated with carbon monoxide gas in the presence of cobalt (II) bromide as described by Devasagayaraj, A. and Knochel, P. Tetrahedron Lett. 36: 8411–8414 (1995) which is incorporated herein by reference in its entirety. In the second method, 4-chloro-1-iodopropane was converted to the corresponding alkyl zinc reagent and then that organo-metallic compound was reacted with the commercially available 5-chloropentanoyl chloride according to the methods described by Klein, H. and Neff, H. Angewante Chemie. 68: 681–682 (1956); by Tamaru, X. et al. Angewante Chemie, International Edition English, 26: 1157–1158, (1987) and by Knoess, H. P. et al. J. Organic Chem. 56: 5974–5978, all three of these references are incorporated herein by reference in their entireties. The final step of this synthesis, replacing the two chlorines with trimethylammonium moieties may be accomplished in quantitative yield by treating nucleoside 3 with a 40% by weight solution of trimethylamine in water.

The present invention includes analogues of the specific nonamethonium ACK compound of the present invention. Thus, an analogue is meant to include a molecule that is structurally similar to the parent molecule (in this case ACK), but different in that chemical groups have been substituted, added, or removed so as to make the analogue structurally distinct from the parent compound.

Pharmacological effects of nonamethonium adenosine cyclic ketal

Preliminary experiments were conducted to evaluate the hemodynamic effects of nonamethonium ACK. Adult male Sprague-Dawley rats utilized in these studies were purchased from Charles River Laboratories (Wilmington, Mass.) and maintained in the University of Pittsburgh Animal Facility. Rats were provided free access to Prolab Isopro RMH 3000 rodent diet (PMI Nutritional Intl., Richmond, Ind.) a nd tap water. The rats weighed approximately 300 grams at the time of study.

Rats were anesthetized with Inactin (100 mg/kg, intraperitoneally or i.p.) and placed on a Deltaphase Isothermal Pad (Braintree Scientific, Inc.; Braintree, Mass.). Body temperature was monitored with a digital rectal probe thermometer (Physioltemp Instruments, Inc.; Clifton, N.J.) and maintained at 37° C. by adjusting a heat lamp above the animal. The trachea was cannulated with polyethylene (PE)-240 to maintain airway patency, a PE-50 catheter was inserted into the left jugular vein and an intravenous infusion of 0.9% saline was initiated at 80 $\mu$l/min. A left carotid artery catheter (PE-50) was inserted and was connected to a digital blood pressure analyzer (Micro-Med; Louisville, Ky.) for continuous measurement of mean arterial blood pressure (MABP) and heart rate. The digital blood pressure analyzer was set to time-average MABP and heart rate at one-minute (slow speed) or two-second (high speed) intervals.

After a 30 minute post-operation rest period, the rats received bolus injections of either adenosine or nonamethonium ACK. Some rats were pretreated with a bolus of 1,3-dipropyl-p-sulfophenylxanthine (DPSPX, a well-characterized adenosine receptor antagonist) followed by a constant rate infusion of DPSPX at 0.15 mg/80 $\mu$l/min. It has previously been shown that this dosing regimen with DPSPX effectively blocks adenosine receptors in the rat in vivo.

FIGS. 2–5 show results from representative experiments described as follows. FIGS. 2A–2B illustrate the effects of a bolus injection of 0.2 mg/kg of adenosine on MABP (FIG. 2A) and on heart rate (FIG. 2B). Adenosine treatment caused profound, rapid and brief hypotensive and bradycardic responses. In this regard, heart rate was reduced by 158 beats per minute as shown in FIG. 2B and MABP was reduced by 76 mm Hg as shown in FIG. 2A. Heart rate recovered in approximately 100 seconds, and MABP recovered in approximately 500 seconds. The faster recovery of heart rate compared with MABP was most likely due to sympathetic activation to the heart caused by the marked hypotension. These experimental data in rats indicated that adenosine caused both hypotension and bradycardia and both effects were rapid in onset and rapid in offset.

Figure 3A:
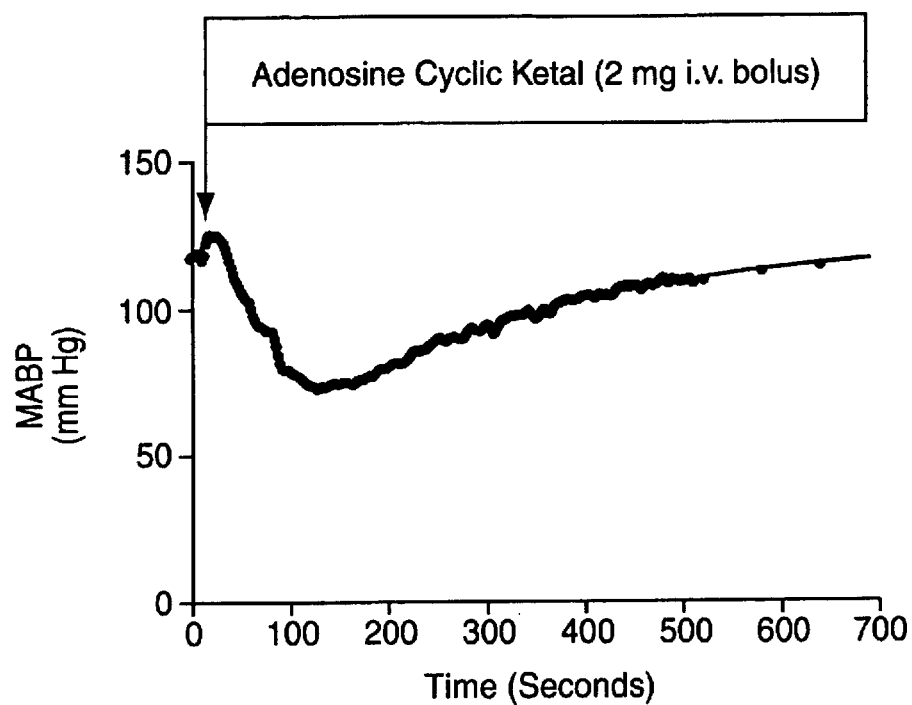
FIG. 3A is a graph illustrating the effects of an intravenous bolus of nonamethonium ACK (2 mg/kg) on mean arterial blood pressure in anesthetized rat.
Figure 3B:
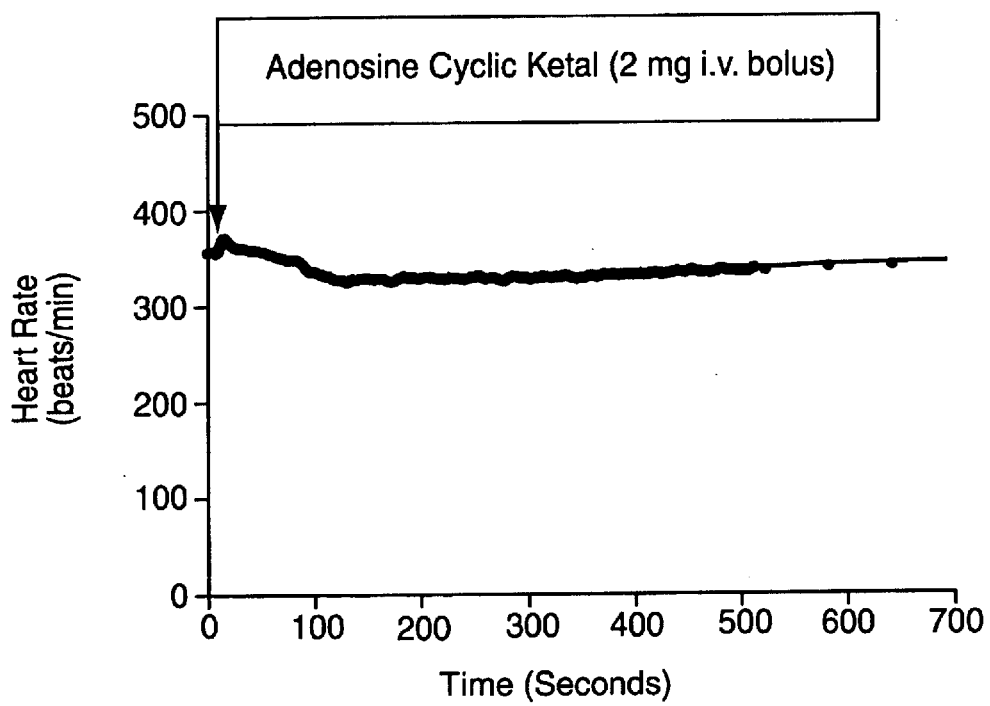
FIG. 3B is a graph illustrating the effects of an intravenous bolus of nonamethonium ACK (2 mg/kg) on heart rate in anesthetized rat.
Figure 4A:
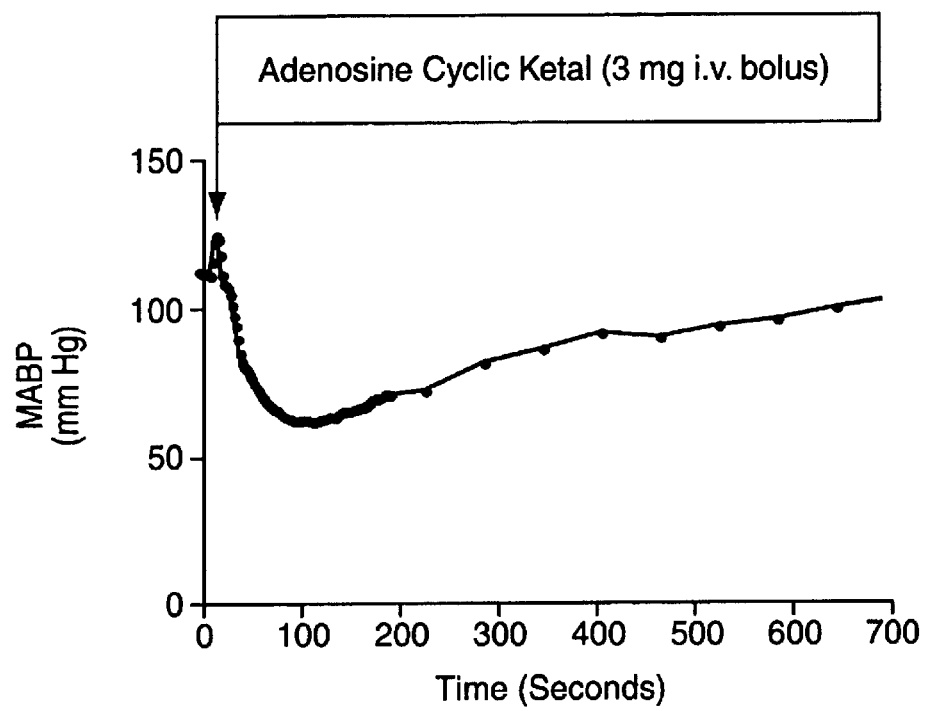
FIG. 4A is a graph illustrating the effects of an intravenous bolus of nonamethonium ACK (3 mg/kg) on mean arterial blood pressure in anesthetized rat.
Figure 4B:
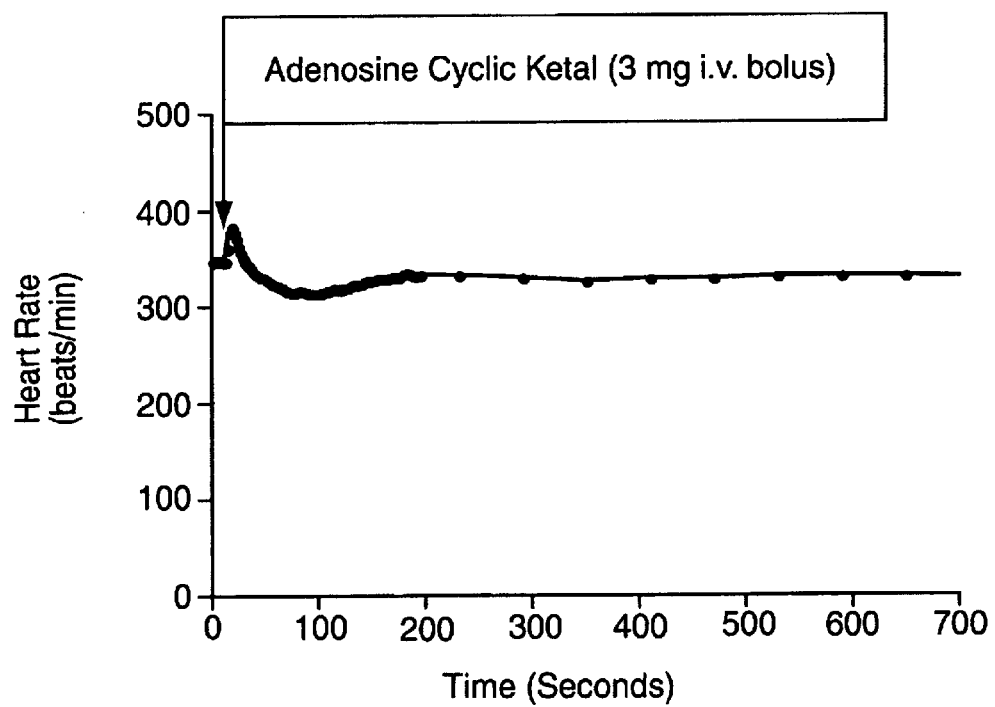
FIG. 4B is a graph illustrating the effects of an intravenous bolus of nonamethonium ACK (3 mg/kg) on heart rate in anesthetized rat.

FIGS. 3A–B and 4A–B illustrate the effects of bolus injections of 2 mg/kg and 3 mg/kg of nonamethonium ACK on MABP and heart rate. Like adenosine treatment, nonamethonium ACK treatment caused a profound, rapid and brief decrease in MABP. In this regard, MABP was decreased by 54 mm Hg by treatment with 2 mg of nonamethonium ACK as shown in FIG. 3A, and by 65 mm Hg by treatment with 3 mg of nonamethonium ACK, as shown in FIG. 4A. As with adenosine treatment, the hypotensive response to nonamethonium ACK treatment was short, i.e., approximately 700 seconds. However, unlike adenosine treatment, administration of nonamethonium ACK did not cause a bradycardic or tachycardic response, as shown in FIG. 3B and FIG. 4B.

The lack of a bradycardic response to nonamethonium ACK indicates that nonamethonium ACK treatment most likely does not activate adenosine $A_1$ receptors. It has been shown in numerous experiments that treatment with adenosine and selective adenosine $A_1$ receptor agonists markedly decreases heart rate in the rat. Moreover, previously published results have shown that bradycardic responses to $A_1$ receptor agonists are entirely blocked by highly selective $A_1$ receptor antagonists such as 1,3-dipropyl-8-p-cyclopentylxanthine and FK453, but not by highly selective $A_2$ receptor antagonists such as KF17837 as described in U.S. Pat. No. 5,861,405 to Jacobson et al. which is hereby incorporated by reference in its entirety.

Since nonamethonium ACK failed to activate $A_1$ receptors, it would be expected that the hypotensive response to nonamethonium ACK would be accompanied by a marked reflex tachycardia. Reflex tachycardia did not occur with nonamethonium ACK. It is likely that nonamethonium ACK is not only an $A_{2A}$ receptor agonist, but also a ganglionic blocker. Thus, the hypotensive response to nonamethonium ACK was not accompanied by an increase in heart rate because autonomic reflexes were inhibited.

Figure 5A:
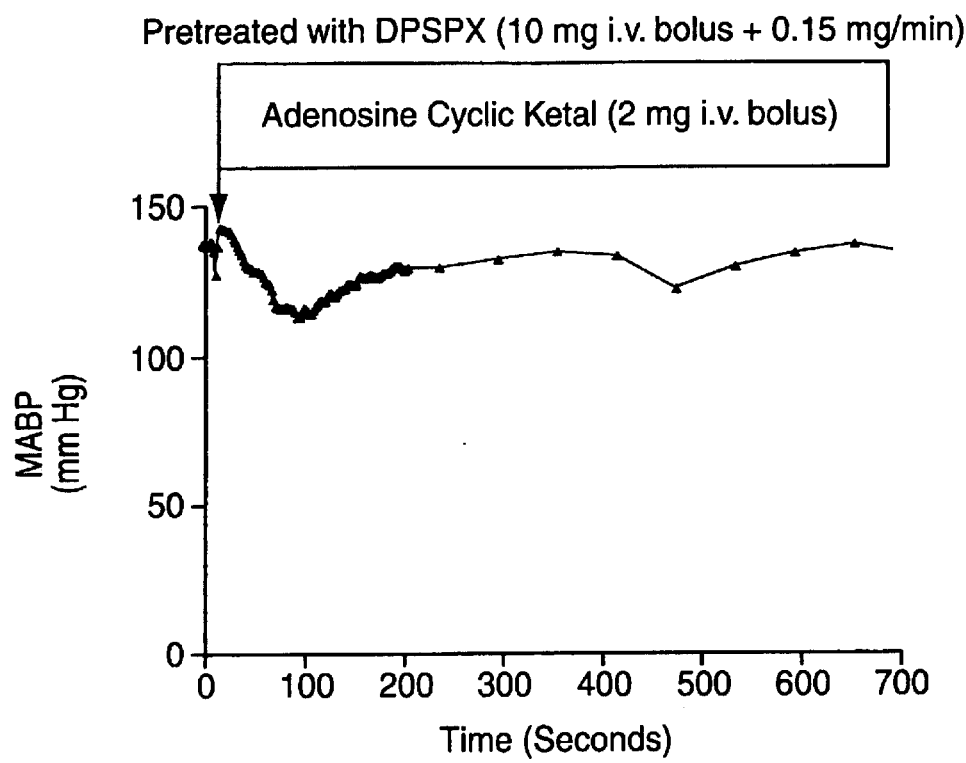
FIG. 5A is a graph illustrating the effects of an intravenous bolus of nonamethonium ACK (2 mg/kg) on mean arterial blood pressure in anesthetized rat pretreated with the adenosine receptor antagonist 1,3-dipropyl-8-p-sulfophenylxanthine (DPSPX)
Figure 5B:
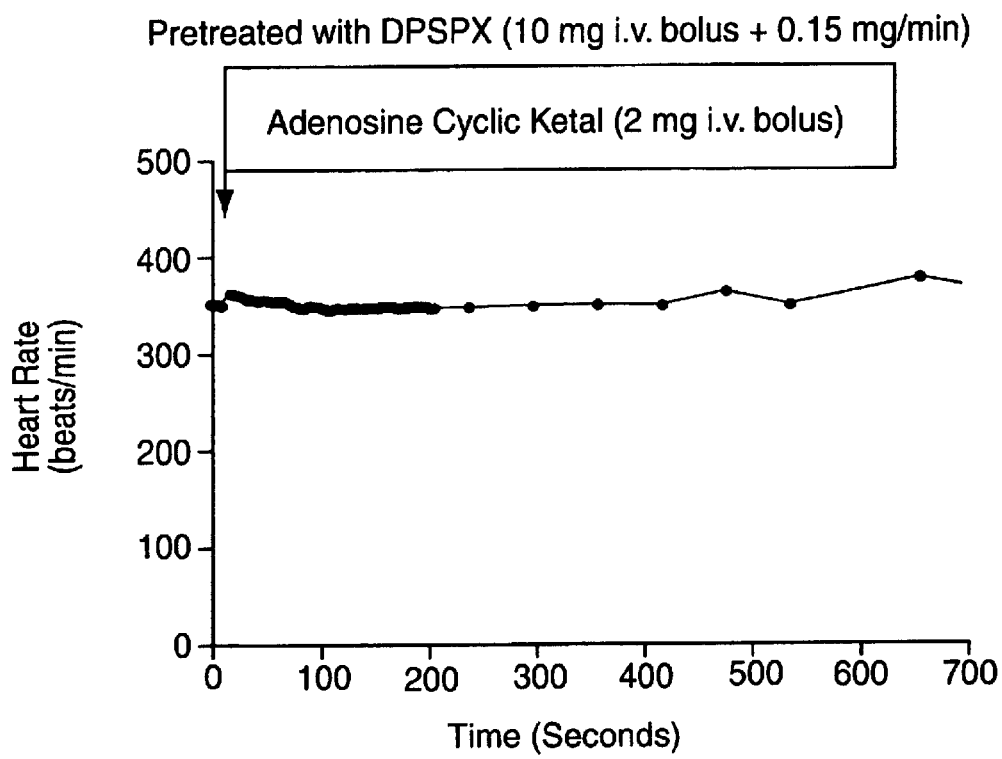
FIG. 5B is a graph illustrating the effects of an intravenous bolus of nonamethonium ACK (2 mg/kg) on heart rate in anesthetized rat pretreated with the adenosine receptor antagonist 1,3-dipropyl-8-p-sulfophenylxanthine (DPSPX).

FIGS. 5A–B illustrate the effects of adenosine receptor antagonism with DPSPX on the hypotensive response to nonamethonium ACK. As shown in FIG. 3A, 2 mg of nonamethonium ACK lowered MABP by a maximum of 54 mm Hg and MABP did not fully recover for approximately 700 seconds. In contrast, in the presence of DPSPX the maximum hypotensive response to nonamethonium was only 24 mm Hg and MABP fully recovered in approximately 200 seconds, as shown in FIG. 5A. Thus, blockade of adenosine receptors both blunted and shortened the response to nonamethonium ACK. This result illustrates that nonamethonium ACK activates $A_{2A}$ adenosine receptors.

To further test the hypothesis that nonamethonium ACK activates $A_{2A}$ adenosine receptors, the effects of nonamethonium ACK on mesenteric vascular resistance were examined. Previous studies have demonstrated that activation of $A_{2A}$ adenosine receptors dilates the mesenteric vascular bed. The following experiments show that nonamethonium ACK dilates gut circulation.

For these experiments, rats were anesthetized with Inactin (100 mg/kg, i.p.) and placed on a Deltaphase Isothermal Pad. Body temperature was monitored with a digital rectal probe thermometer and maintained at 37° C. by adjusting a heat lamp above the animal. The trachea was cannulated with PE-240 to maintain airway patency, a PE-50 catheter was inserted into the left jugular vein and an intravenous infusion of 0.9% saline was initiated at 50 $\mu$l/min. A left carotid artery catheter (PE-50) was inserted and was connected to a digital blood pressure analyzer for continuous measurement of MABP and heart rate. The digital blood pressure analyzer was set to time-average MABP and heart rate at two-minute intervals. A transit-time blood flow probe (model 1RB; Transonic Systems Inc., Ithaca, N.Y.) was placed around the superior mesenteric artery and connected to a transit-time flowmeter (model T206; Transonic Systems, Inc.) to monitor mesenteric blood flow (MBF) continuously. A 32-gauge needle connected to a PE-10 catheter was inserted (proximal to the flow probe) into the superior mesenteric artery, and an intramesenteric artery infusion of 0.9% saline (50 $\mu$l/min) was initiated. The rats were allowed to stabilize for approximately one hour after the surgical preparation was completed.

The abdominal skin and muscle flaps around the midline incision were supported in a bowl-shaped fashion to create a basin containing all of the viscera, and 40 ml of 0.9% saline prewarmed to 37° C. was instilled into the peritoneal cavity. The small and large intestines were submerged entirely in the peritoneal lavage fluid. MABP and heart rate were time averaged (1100 Hz) over the last six minutes of the first 15-minute experimental period, and three readings of MBF were taken at two-minute intervals over the last six minutes of the first 15-minute experimental period and averaged.

Next, angiotensin II (30 ng/min; a powerful vasoconstrictor) plus methoxamine (3 $\mu$g/min; an alpha-1 adrenoreceptor agonist and vasoconstrictor) were infused into the superior mesenteric artery (50 $\mu$l/min). This infusion was maintained for the duration of the experiment. The purpose of the infusion of angiotensin II and methoxamine was to increase mesenteric vascular tone so that the effects of a vasodilator could be more easily observed. Again, MABP, heart rate and MBF were recorded as described above during the last six minutes of the second 15-minute experimental period.

At this stage, the rats were divided into two groups. In all groups, three additional back-to-back 15-minute experimental periods were conducted in which MABP, heart rate and MBF were recorded during the last six minutes of each period. However, in one group, the peritoneal lavage fluid was changed to a saline solution containing nonamethonium ACK (1 mM); whereas in the second group, the peritoneal lavage fluid was changed to saline lacking nonamethonium ACK. Direct application of nonamethonium ACK to the gut, rather than intravenous or intra-arterial infusion, was employed to prevent confounding effects of nonamethonium ACK-induced hypotension. In this regard, since nonamethonium ACK carried two fixed positive charges, it was reasoned that systemic absorption would be minimal and thus systemic hypotension would be minimal.

Figure 6A:
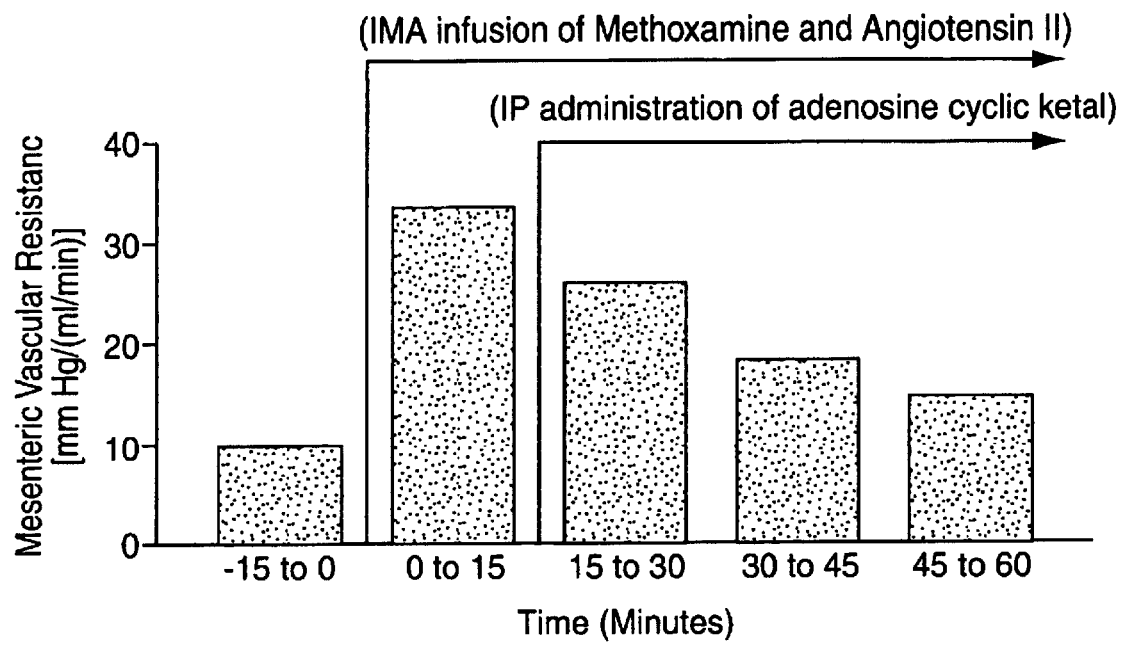
FIG. 6A is a bar graph showing the effect of an intraperitoneal administration of nonamethonium ACK (1 mM) or of saline (shown in FIG. 6B) on mesenteric vascular resistance. Similar findings were obtained with adenosine (1 mM); data not shown.
Figure 6B:
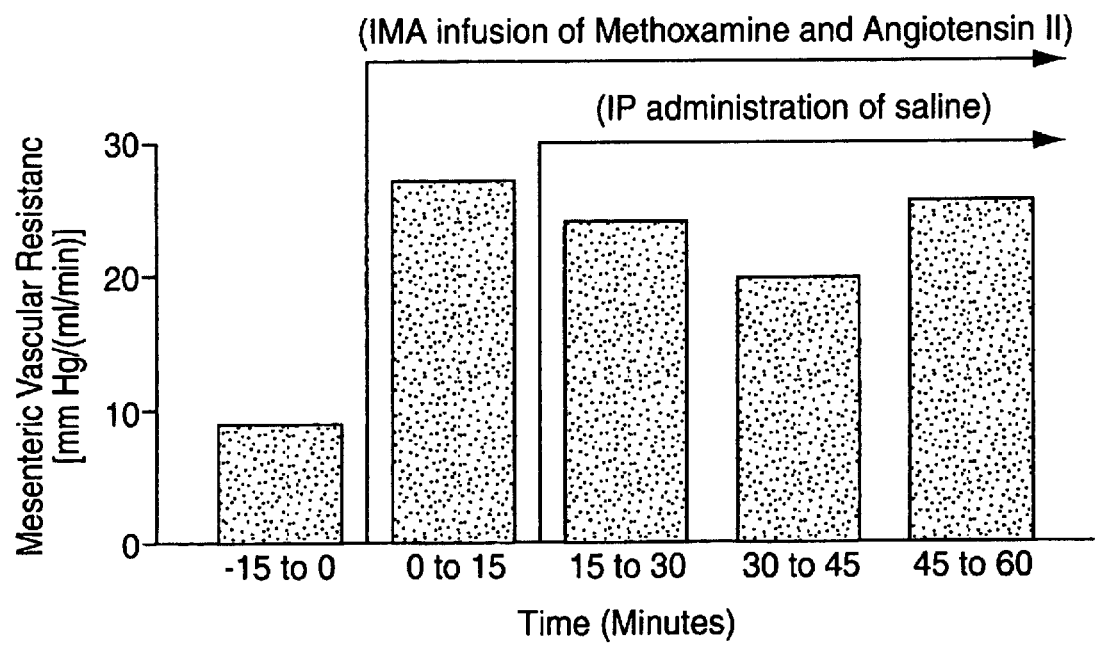

As illustrated in FIG. 6A, an intramesenteric infusion of angiotensin II and methoxamine increased mesenteric vascular resistance by three-fold. Application of nonamethonium ACK reduced mesenteric vascular resistance to basal levels, i.e., the vasoconstriction induced by angiotensin II and methoxamine was completely overcome. In contrast, application of saline (FIG. 6B) did not significantly alter mesenteric vascular resistance. As expected, the intraperitoneal application of nonamethonium ACK had no effect on MABP. Thus, these results show that nonamethonium ACK, like other $A_{2A}$ receptor agonists, has the ability to vasodilate the gut circulation via a direct effect. These results are further evidence that nonamethonium ACK is an effective $A_{2A}$ receptor agonist.

The present invention provides a new class of adenosine analogues in which both the 2' and 3' positions are modified in such a manner as to retain biological activity.

The need for agents such as ACKs of the present invention is great and increasing. An important example is in diagnostic cardiology. In this regard, coronary vasodilation increases coronary blood flow, thus creating differences in the distribution of cardiac perfusion imaging agents great enough to identify regions supplied by stenosed coronary vessels and to distinguish infarct from noninfarct areas. Exercise stress testing is often employed for dilating coronary vessels, hence increasing coronary blood flow. However, maximal exercise levels are required for sufficient vasodilation, and exercise capacity varies greatly among patients. Additionally, exercise is not an option for many patients since arthritis, peripheral vascular disease, Parkinson's disease, amputations, medications and poor patient health and motivation may preclude many patients from exercising at maximal levels. As the general population ages, the prevalence of ischemic heart disease increases and, at the same time, the percentage of patients requiring pharmacological stress testing, as opposed to physiological stress testing, increases.

In addition to diagnostic cardiology, an aging population also increases the need for rapid onset/rapid offset vasodilators, such as the ACK analogues of the present invention, for the acute induction of controlled hypotension during surgical treatment of dissecting aortic aneurysms, intracranial aneurysms, tumors and prostatic disease. Pharmacological methods for safe and effective controlled hypotension in order to limit intraoperative blood loss and avoid the need for homologous transfusion are greatly needed and are provided by embodiments of the present invention.

The medical applications of ACK analogues may also extend beyond hypertensive crises, controlled hypotension and diagnostic cardiology. A recent study (phase II clinical trial) demonstrates that a three-hour intravenous infusion of adenosine reduces infarct size by 66% in patients with acute anterior myocardial infarction. Currently, two phase III clinical trials are underway (AMISTAD II in the USA and LISA in France) in an attempt to achieve regulatory approval of intravenous adenosine for heart attacks. It is likely that ACK analogues will find utility in the treatment of myocardial ischemia/reperfusion injury in patients with acute myocardial infarction. Thus, the medical uses for ACK analogues could extend to millions of people worldwide.

Details on techniques for formulation and administration of pharmaceuticals useful in the preparation and/or use of the compounds of the present invention may be found in the latest edition of *Remington's Pharmaceutical Sciences* (Mack Publishing Co., Easton, Pa.). As used herein, the terms "therapeutic" and/or "effective" amounts mean an agent utilized in an amount sufficient to treat, combat, ameliorate, prevent or improve a condition or disease of a patient. Determining whether improvements in conditions are being achieved may require obtaining periodic indicators of such responses as $A_{2A}$ receptor activation and/or blocking of the activity of the autonomic nervous system, as manifested in changes in disease conditions that can be monitored by blood pressure and/or heart rate. These disease conditions include hypertension, ischemia and/or ischemic damage as well as any condition where vasodilation is affected.

Analogues of ACK may be administered orally, for example, with an inert diluent, typically an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, waters, chewing gums, and the like. The amount of the compounds consisting of embodiments of the present invention will be such that a suitable dosage will be provided in the administered amount.

Tablets, pills, capsules, troches and the like may contain the following ingredients: a binder, such as micro-crystalline cellulose, gum tragacanth or gelatin; an excipient, such as starch or lactose; a disintegrating agent, such as alginic acid, Primogel, corn starch and the like; a lubricant, such as magnesium stearate or Sterotes; a glidant, such as colloidal silicon dioxide; a sweetening agent, such as sucrose, saccharin or aspartame; or flavoring agent, such as peppermint, methyl salicylate or orange flavoring. When the dosage unit form is a capsule it may contain, in addition to compounds comprising embodiments of the present invention, a liquid carrier, such as a fatty oil. Other dosage unit forms may contain other materials that modify the physical form of the dosage unit, for example, as coatings. Thus, tablets or pills may be coated with sugar, shellac or other enteric coating agents. A syrup may contain, in addition to the active compounds, sucrose as a sweetening agent and preservatives, dyes, colorings and flavors. Materials used in preparing these compositions should be pharmaceutically pure and non-toxic in the amounts used.

For purposes of parenteral therapeutic administration, the ACK analogues may be incorporated into a solution or suspension. The amount of active compound in such compositions is such that a suitable dosage will be obtained.

Solutions or suspensions of analogues of ACK may also include the following components: a sterile diluent, such as water for injection, saline solution, fixed oils, polyethylene glycols, glycerine, propylene glycol or other synthetic solvents: antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity or osmolarity, such as sodium chloride or dextrose. The parenteral preparation may be enclosed in ampoules, disposable syringes or multiple dose vials made of glass or plastic.

It is to be understood that ACK analogues may be administered in the form of a pharmaceutically acceptable salt. Examples of such salts include acid addition salts. Preferred pharmaceutically acceptable addition salts include salts of mineral acids, for example, salts of hydrochloric acid, sulfuric acid, nitric acid and the like; salts of monobasic carboxylic acids, such as, for example, acetic acid, propionic acid and the like; salts of dibasic carboxylic acids, such as maleic acid, fumaric acid, oxalic acid and the like; and salts of tribasic carboxylic acids, such as, carboxysuccinic acid, citric acid and the like. In ACK analogues in which an [R] is [- - - $CO_2$ H], the salt may be to derived by replacing the acidic proton of the [- - - $CO_2$ H] group with a cation such as $Na^+$, $K^+$, $NH_4^+$, mono-, di-, tri-, or tetra ($C_{1-4}$ -alkyl)ammonium, or mono-, di-, tri-, or tetra($C_{2-4}$ -alkanol) ammonium.

It is also to be understood that analogues of ACK may exist as various isomers, enantiomers and diastereomers and that the present invention encompasses the administration of a single isomer, enantiomer or diastereomer in addition to the administration of mixtures of isomers, enantiomers or diastereomers. Additionally, analogues of ACK may be administered either alone or in combination with other therapeutic compositions in order to achieve the desired, improved conditions in the subject in need thereof.

It is to be understood, however, that for any particular subject, specific dosage regimens should be adjusted to the individual need and the professional judgement of the person administering or supervising the administration of the compound. The term "subject" as used herein means any mammal, including humans, where $A2_A$ receptor activation occurs. The methods herein for use on subjects/patients contemplate prophylactic as well as curative use in therapy of an existing condition.

The preferred mode of administration of ACK analogues may also depend on the exact condition being treated. The mode of administration may include by tablet (oral dose form) or by intravenous, parenteral, subcutaneous, intramuscular injection, topical application or instillation into a body cavity.

The exact dosage of ACK analogues to be administered will, of course, depend on the size and condition of the patient being treated, the exact condition being treated and the identity of the particular ACK analogue being administered.

Inasmuch as the compounds of the present invention are useful as cardiac vasodilators, cardiovascular and particularly as anti-hypertensive agents in mammals, various modes of administering the compounds to domestic animals and humans in particular will be apparent to one of ordinary skill in the art. Such modes of administering compounds of the present invention include oral and topical administration and intravenous infusion. One having average skill in the art may readily prepare suitable formulations for the above-mentioned and other modes of administering the compounds of the present invention. The total daily dose may be given as a single dose, multiple doses, e.g., two to six times per day, or by intravenous infusion for a selected duration.

It will be appreciated by those skilled in the art that the invention may be practiced within a wide range of equivalent parameters, concentrations and conditions without departing from the spirit and scope of the invention and without undue experimentation. While this invention has been described in connection with specific embodiments thereof, it will be understood that it is capable of further modifications. This application is intended to cover any variations, uses or adaptations of the inventions following, in general, the principles of the invention and including such departures from the present disclosure as come within known or customary practice within the art to which the invention pertains.

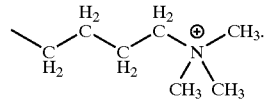

What is claimed is:

1. A compound of the formula:

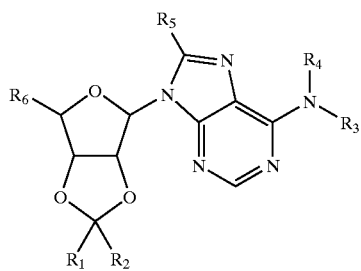

$R_1$ and $R_2$ are each an amine group or an alkylamine group;
further wherein $R_3$, $R_4$, and $R_5$ are each a hydrogen or a halogen;
further wherein $R_6$ is an alkyl alcohol group or a carboxamido group;
or a pharmaceutically acceptable salt thereof.

2. The compound of claim 1, wherein $R_1$ and $R_2$ each contain one to thirteen carbons.

3. The compound of claim 1, wherein the amine group is on a terminal carbon.

4. The compound of claim 1, wherein said halogen is selected from the group consisting of fluorine, chlorine and bromine.

5. The compound of claim 1, wherein $R_6$ is selected from the group consisting of methyl alcohol, ethyl alcohol, isopropyl alcohol and n-propyl alcohol.

6. The compound of claim 1, wherein $R_6$ is a N-alkylcarboxamido group selected from the group consisting of N-methylcarboxamido, N-ethylcarboxamido, N-isopropylcarboxamido, and N-n-propylcarboxamido.

7. The compound of claim 1, wherein said amine group is selected from the group consisting of primary amine, secondary amine and tertiary amine.

8. The compound of claim 1, wherein $R_1$ and $R_2$ are each:

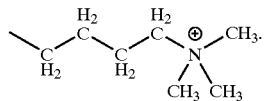

9. A compound of the formula:

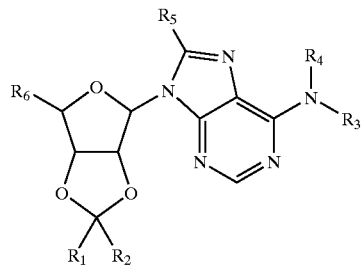

wherein $R_1$, $R_2$, are each:

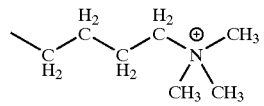

$R_3$, $R_4$, and $R_5$ are each hydrogen;
and $R_6$ is:

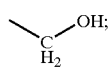

or a pharmaceutically acceptable salt thereof.

10. A pharmaceutical composition for the treatment of hypertension comprising an effective amount of a compound of the formula:

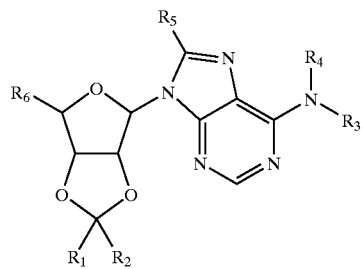

wherein $R_1$ and $R_2$ are each an amine group or an alkylamine group;
further wherein $R_3$, $R_4$, and $R_5$ are each a hydrogen or a halogen;
further wherein $R_6$ is an alkyl alcohol group or a carboxamido group;
or a pharmaceutically acceptable salt thereof;
and a pharmaceutically acceptable carrier.

11. The pharmaceutical composition of claim 10, wherein $R_1$ and $R_2$ each contain one to thirteen carbons.

12. The pharmaceutical composition of claim 10, wherein said amine group is selected from the group consisting of primary amine, secondary amine and tertiary amine.

13. The pharmaceutical composition of claim 10, wherein said amine group is on a terminal carbon.

14. The pharmaceutical composition of claim 10, wherein said halogen selected from the group consisting of fluorine, chlorine and bromine.

15. The pharmaceutical composition of claim 10, wherein said alkyl alcohol group is selected from the group consisting of methyl alcohol, ethyl alcohol, isopropyl alcohol and n-propyl alcohol.

16. The pharmaceutical composition of claim 10, wherein $R_6$ is a N-alkylcarboxamido group selected from the group consisting of N-methylcarboxamido, N-ethylcarboxamido, N-isopropylcarboxamido and N-n-propylcarboxamido.

17. The pharmaceutical composition of claim 10, wherein $R_1$ and $R_2$ are each: